(12) United States Patent
Kroll

(10) Patent No.: US 7,113,822 B1
(45) Date of Patent: *Sep. 26, 2006

(54) SYSTEM AND METHOD FOR PROVIDING CARDIOVERSION THERAPY AND OVERDRIVE PACING USING AN IMPLANTABLE CARDIAC STIMULATION DEVICE

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 521 days.

This patent is subject to a terminal disclaimer.

(21) Appl. No.: 10/374,835

(22) Filed: Feb. 25, 2003

(51) Int. Cl.
*A61N 1/39* (2006.01)

(52) U.S. Cl. .................. 607/4; 607/9; 607/14; 607/15
(58) Field of Classification Search .............. 607/4, 607/5, 14, 15
See application file for complete search history.

(56) References Cited

U.S. PATENT DOCUMENTS

| | | | |
|---|---|---|---|
| 5,314,448 A | 5/1994 | Kroll et al. ............ 607/5 |
| 5,366,485 A | 11/1994 | Kroll et al. ............ 607/5 |
| 5,411,524 A | 5/1995 | Rahul ................. 607/4 |
| 5,562,708 A * | 10/1996 | Combs et al. .......... 607/4 |
| 5,676,687 A * | 10/1997 | Ayers ................. 607/4 |
| 5,713,924 A | 2/1998 | Min et al. ............. 607/4 |
| 5,713,929 A * | 2/1998 | Hess et al. ........... 607/14 |
| 5,906,633 A * | 5/1999 | Mouchawar et al. ...... 607/5 |
| 6,081,746 A | 6/2000 | Pendekanti et al. ...... 607/5 |
| 6,091,989 A * | 7/2000 | Swerdlow et al. ....... 607/5 |
| 6,097,983 A | 8/2000 | Strandberg ............ 607/9 |
| 6,185,459 B1 * | 2/2001 | Mehra et al. .......... 607/14 |
| 6,208,902 B1 | 3/2001 | Boveja ............... 607/46 |
| 6,249,699 B1 | 6/2001 | Kim .................. 607/4 |
| 6,292,691 B1 | 9/2001 | Pendekanti et al. ..... 607/4 |
| 6,351,669 B1 | 2/2002 | Hartley et al. ......... 607/5 |
| 6,438,418 B1 | 8/2002 | Swerdlow et al. ....... 607/5 |
| 6,445,949 B1 | 9/2002 | Kroll ................. 607/4 |
| 6,456,876 B1 | 9/2002 | Kroll ................. 607/4 |
| 6,510,342 B1 | 1/2003 | Park et al. ............ 607/15 |
| 6,813,516 B1 * | 11/2004 | Ujhelyi et al. ......... 607/4 |
| 6,829,504 B1 | 12/2004 | Chen et al. ........... 607/4 |
| 2004/0049232 A1 * | 3/2004 | Ideker et al. .......... 607/4 |
| 2004/0088010 A1 * | 5/2004 | Warman et al. ......... 607/5 |

* cited by examiner

*Primary Examiner*—Robert Pezzuto
*Assistant Examiner*—Yun Haeng Lee

(57) ABSTRACT

Techniques are provided for coordinating the delivery of cardioversion therapy and overdrive pacing therapy to the heart of a patient, primarily to prevent the re-occurrence of atrial fibrillation (AF) following a cardioversion shock. Included are techniques for modulating the aggressiveness of overdrive pacing by adjusting the magnitude of overdrive pulses or by changing the electrodes with which overdrive pacing pulses are generated. In one example, three phases or "tiers" of AF suppression therapy are provided: cardioversion therapy; far-field dynamic atrial overdrive (DAO) pacing; and near-field DAO pacing. Briefly, a cardioversion shock is delivered to the heart of the patient in response to the detection of AF, then smoothed, far-field overdrive pacing pulses are delivered using widely-spaced electrodes for a period of two minutes while the magnitude of the pulses is gradually reduced. Finally, near-field overdrive pacing pulses are delivered more or les continuously until another episode of AF is detected.

17 Claims, 6 Drawing Sheets

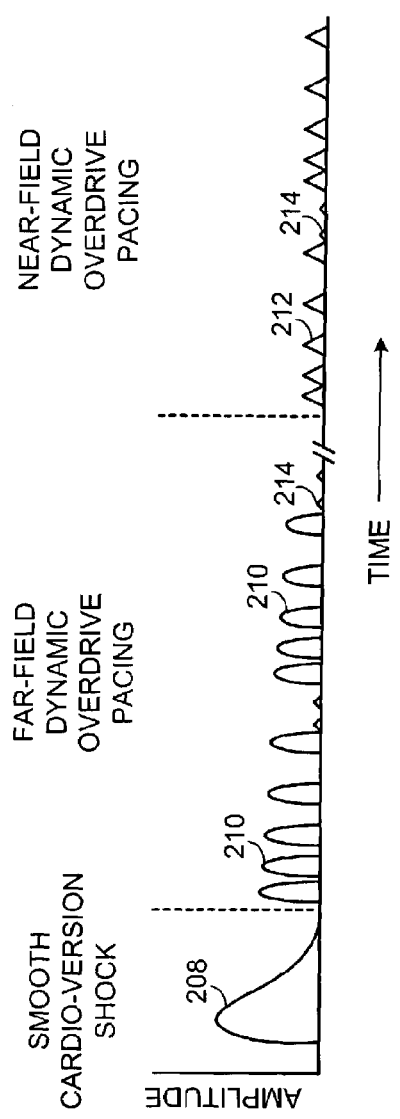
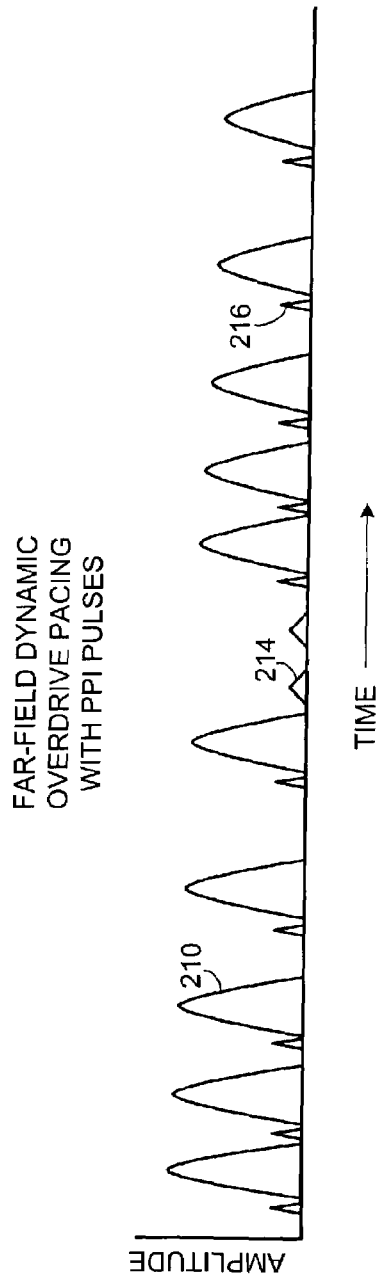

SYSTEM AND METHOD FOR PROVIDING CARDIOVERSION THERAPY AND OVERDRIVE PACING USING AN IMPLANTABLE CARDIAC STIMULATION DEVICE

CROSS-REFERENCE TO RELATED APPLICATIONS

This application is related to copending U.S. patent Application Ser. No. 10/374,489, entitled "System and Method for Providing Cardioversion Therapy and Overdrive Pacing Using an Implantable Cardiac Stimulation Device," filed Feb. 25, 2003.

FIELD OF THE INVENTION

The invention generally relates to implantable cardiac stimulation devices such as implantable cardioverter/defibrillators (ICDs) and pacemakers and, in particular, to techniques for providing cardioversion therapy and overdrive pacing therapy using implantable cardiac stimulation devices.

BACKGROUND OF THE INVENTION

Atrial fibrillation (AF) is a type of tachycardia wherein the atria of the heart beats chaotically, thus interfering with efficient cardiac function. Although not fatal, AF can trigger ventricular fibrillation (VF), wherein the ventricles beat chaotically such that there is little or no net flow of blood from the heart to the brain and other organs. VF, if not terminated, is fatal. Hence, it is highly desirable to prevent or terminate AF and VF.

One technique for preventing AF or VF using a pacemaker is to pace chambers of the heart at a rate somewhat faster than the intrinsic heart rate of the patient using a technique referred to as overdrive pacing. Overdrive pacing may be applied to the atria or the ventricles. A particularly effective overdrive pacing technique for the atria, referred to herein as dynamic atrial overdrive (DAO) pacing, is described in U.S. Pat. No. 6,519,493 of Florio et al., entitled "Methods And Apparatus For Overdrive Pacing Heart Tissue Using An Implantable Cardiac Stimulation Device", issued Feb. 11, 2003. With DAO, the overdrive pacing rate is controlled to remain generally uniform and, in the absence of a tachycardia, is adjusted upwardly or downwardly only occasionally. The aggressiveness of overdrive pacing may be modulated by adjusting the overdrive pacing rate and related control parameters. See: U.S. patent application Ser. Nos. 10/093,225 and 10/092,695, both of Florio et al., entitled "Method And Apparatus For Using A Rest Mode Indicator To Automatically Adjust Control Parameters Of An Implantable Cardiac Stimulation Device", and both filed Mar. 6, 2002; U.S. patent application Ser. No. 10/043,781, also of Florio et al., entitled "Method And Apparatus For Dynamically Adjusting A Non-Linear Overdrive Pacing Response Function", filed Jan. 9, 2002; and U.S. patent application Ser. No. 10/043,472, of Falkenberg et al., entitled "Method And Apparatus For Dynamically Adjusting Overdrive Pacing Parameters", filed Jan. 9, 2002. Capture of overdrive pulses may be verified as set forth in U.S. patent application Ser. No. 10/138,438, of Bradley et al., entitled "Method And Apparatus For Providing Atrial AutoCapture In A Dynamic Atrial Overdrive Pacing System For Use In An Implantable Cardiac Stimulation Device", filed May 2, 2002. Each of the aforementioned patent applications is incorporated herein in their entirety.

It is believed that DAO and DVO are effective for at least some patients for preventing AF and VF for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods, which, in turn, can trigger a tachycardia such as fibrillation. By overdrive pacing the heart at a generally uniform rate slightly above the intrinsic rate, the likelihood of the occurrence of ectopic pulses is reduced, the refractory periods within the heart tissue are rendered more uniform and periodic and the heart is thereby resynchronized. Hence, the dispersion of refractory periods is reduced and the risk of AF or VF is reduced.

Thus, overdrive pacing, particularly DAO and DVO, provides a useful technique for helping to prevent the onset of a tachycardia such as fibrillation. As noted, the aggressiveness of overdrive pacing may be adjusted by modulating the overdrive pacing rate and related control parameters. Circumstances may arise, however, where it is desirable to modulate the aggressiveness of overdrive pacing by instead adjusting the magnitude of the overdrive pulses or by changing the electrodes with which the pacing pulses are delivered to the heart. For example, there may be a need to ensure that the overdrive pulses are captured in a larger portion of heart tissue so as to achieve enhanced resynchronization. Aspects of the invention are directed to this end. In particular, it would be desirable to provide at least two "tiers" of overdrive pacing therapy, employing different pulse magnitudes and different electrode combinations, to thereby allow the scope of pulse capture to be controlled.

Whereas overdrive pacing is primarily directed to preventing tachycardias such as AF from arising, cardioversion is employed to terminate AF once it has occurred. Patients prone to AF may have an ICD implanted therein that is capable of detecting AF and automatically administering one or more cardioversion shocks in an effort to revert the atria to a normal sinus rhythm. Typically, the ICD administers about two joules of energy directly to the atria in each cardioversion shock. Cardioversion techniques are described in U.S. Pat. No. 6,445,949 to Kroll, entitled "Implantable Cardioversion Device with a Self-Adjusting Threshold for Therapy Selection", which is incorporated by reference herein.

Although cardioversion is effective in terminating AF, in many cases fibrillation soon returns, requiring another round of shocks. Repeated shocks are quite painful and can deplete battery resources of the implanted device. One reason cardioversion shocks are painful is that the patient is typically conscious and alert at the time the shock is administered. This is in contrast with much stronger defibrillation shocks provided for terminating VF, which are typically not administered until the patient has lost consciousness. Because AF is not usually immediately life threatening, painful shocks for its treatment may be perceived by patients as worse than the disease itself and therefore not tolerated. Indeed, anxiety arising in a patient from the fear of receiving multiple, painful cardioversion shocks may be sufficient to raise the heart rate sufficiently to trigger such shocks.

As some patients have hundreds of AF episodes annually, it would be highly desirable to provide techniques for preventing the re-occurrence of AF following a cardioversion shock so as to reduce the need for multiple, repeated cardioversion shocks. It is to this end that other aspects of the invention are directed. In particular, it would be desirable to provide techniques for coordinating the delivery of cardioversion therapy and overdrive pacing therapy so as to prevent the re-occurrence of AF following a cardioversion shock.

SUMMARY

In accordance with a first embodiment, a system and method is provided for delivering both cardioversion therapy and overdrive pacing therapy to the heart of a patient using an implantable cardiac stimulation device. Briefly, cardioversion therapy is delivered to the heart using a cardioversion shock system, and then overdrive pacing therapy is delivered, substantially immediately following the cardioversion therapy, using an overdrive pacing system. By commencing overdrive pacing promptly following cardioversion therapy, the risk of immediate re-occurrence of fibrillation is believed to be substantially reduced.

In accordance with a second embodiment, a system and method is provided for delivering both far-field and near-field overdrive pacing therapy to the heart of a patient using an implantable cardiac stimulation device. Far-field therapy (or "global therapy") is delivered, for example, using an electrode mounted in the heart in combination with the device body or housing to ensure that the overdrive pacing pulses are captured throughout a large portion of heart tissue to maximize effectiveness. Near-field therapy (or "local therapy") is delivered, for example, using a pair of electrodes that are both mounted in the heart, thus providing for capture within a smaller portion of heart tissue so as to allow for reduced power consumption and reduced patient discomfort. By providing for both far-field (global) and near-field (local) overdrive pacing, the more aggressive far-field pacing may be performed when needed to resynchronize chambers of the heart, such as immediately following cardioversion therapy, whereas the less aggressive near-field therapy may be performed at all other times.

In an exemplary embodiment, wherein the implantable device is an ICD configured to provide DAO therapy, both aspects of the invention are implemented, i.e., upon detection of AF, the device provides cardioversion therapy, followed by far-field DAO therapy, followed by near-field DAO therapy. Hence, "triple-tiered" AF therapy is provided. By providing triple-tiered AF therapy, enhanced AF suppression is achieved. Near-field DAO pacing is performed more or less continuously to reduce the risk of onset of AF. Should AF nevertheless occur, cardioversion shocks are delivered to terminate AF, then far-field DAO pacing is performed to help resynchronize the atria and prevent an immediate re-occurrence of AF. Far-field DAO is performed for about two minutes immediately following the cardioversion shocks, then near-field DAO pacing resumes.

In one particular example, far-field DAO pacing is provided using the right atrial coil electrode in combination with either the device housing or ring electrodes mounted in the proximal coronary sinus. This helps ensure that the far-field DAO pulses capture throughout most of the atria without also pacing the ventricles. Near-field DAO pacing uses otherwise conventional atrial tip-ring electrode combinations. The pulse magnitudes of the far-field pulses decrease gradually during far-field DAO from an initial magnitude such as 20–25 volts down to a lower magnitude, such as 5–10 volts. Near-field DAO uses only low-magnitude pulses, such as 5 volts. Cardioversion therapy employs one or more cardioversion shocks having smoothed shapes to reduce patient discomfort. The far-field DAO pulses also have smoothed shapes to reduce patient discomfort and are each preceded by a pre-pulse inhibition (PPI) pulse provided to further reduce pain. Alternatively, or additionally, transcutaneous electric nerve stimulation (TENS) or neuro-electric acupuncture techniques (NEAP) are employed internally to reduce pain.

Thus various techniques are provided for coordinating the delivery of cardioversion therapy and overdrive pacing therapy so as to prevent the re-occurrence of AF following a cardioversion shock, including techniques for modulating the aggressiveness of overdrive pacing by adjusting the magnitude of overdrive pulses and by changing the electrodes with which the pacing pulses are delivered to the heart. Other features, objects and advantages of the invention are set forth below.

BRIEF DESCRIPTION OF THE DRAWINGS

Further features and advantages of the invention may be more readily understood by reference to the following description taken in conjunction with the accompanying drawings, in which:

FIG. 5 is a graph illustrating three phases of AF suppression therapy provided in accordance with the method of FIG. 4 including cardioversion, far-field DAO and near-field DAO;

FIG. 7 is a graph illustrating far-field DAO pacing with PPI pulses provided in accordance with the method of FIG. 6.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
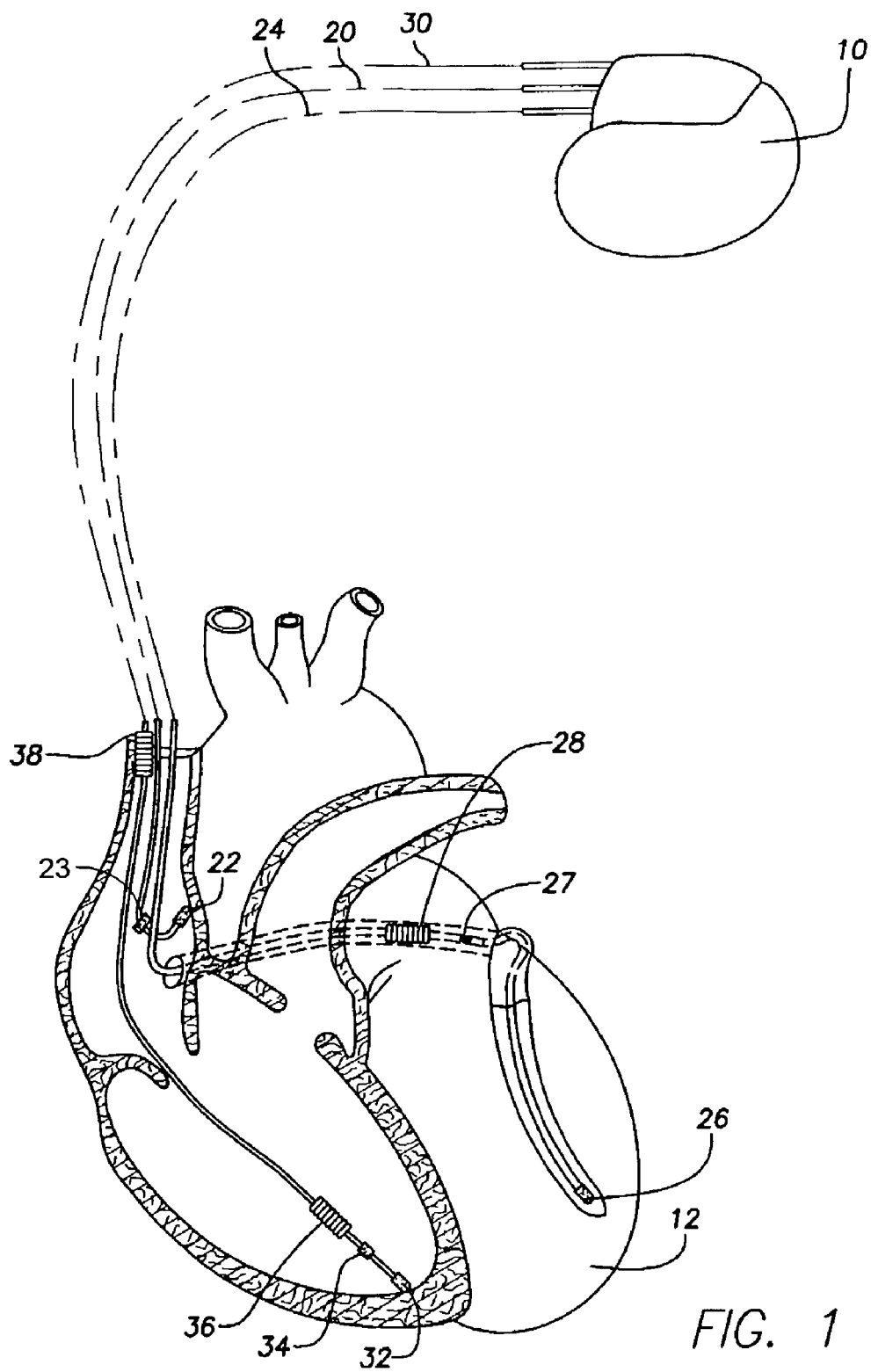
FIG. 1 is a simplified diagram illustrating an implantable stimulation device in electrical communication with at least three leads implanted into the heart of a patient for delivering multi-chamber stimulation and shock therapy including cardioversion therapy and overdrive pacing therapy.

As shown in FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38, also referred to as a right atrial coil electrode. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle.

Figure 2:
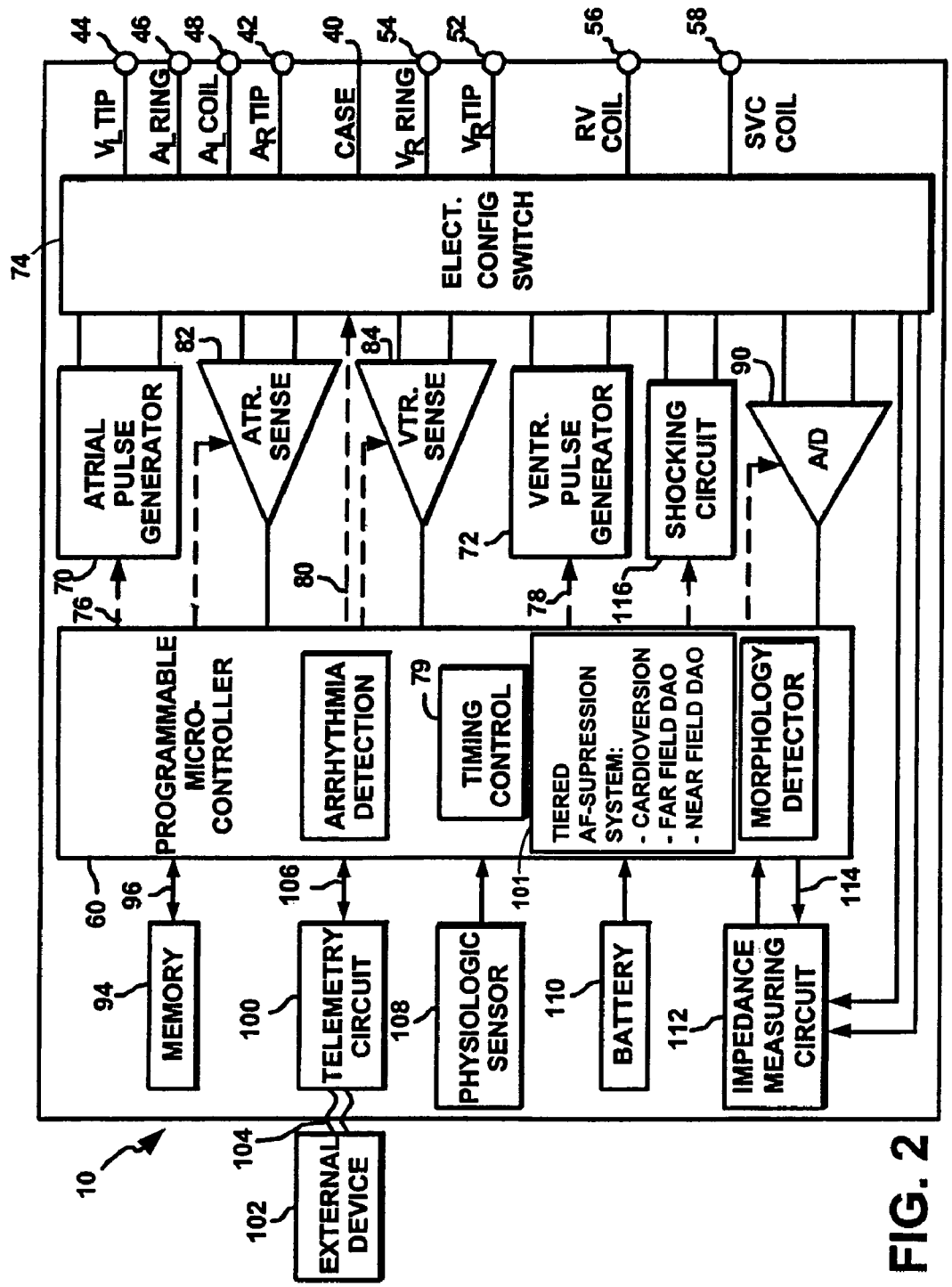
FIG. 2 is a functional block diagram of the implantable cardiac stimulation device of FIG. 1 illustrating basic elements of a stimulation device including a tiered AF suppression system for coordinating the delivery of cardioversion therapy and overdrive pacing therapy.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 6Q may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Figure 3:
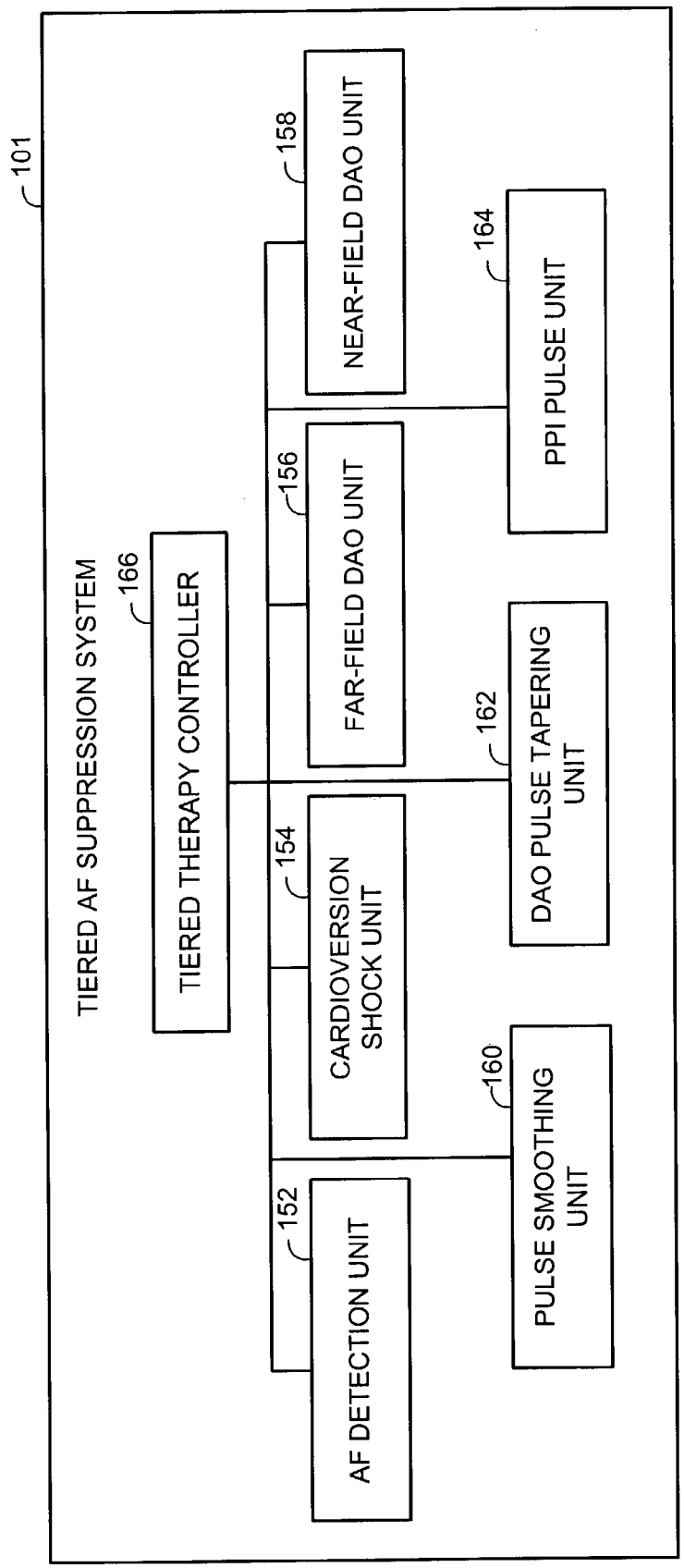
FIG. 3 is a functional block diagram of components of the tiered AF suppression system of FIG. 2.

The microcontroller also includes a tiered AF suppression system 101, which provides for cardioversion therapy, far-field DAO therapy and near-field DAO therapy. Individual components of AF suppression system 101 are shown in FIG. 3 and their operation is described with reference to FIGS. 4–7. During near-field DAO pacing or whenever DAO pacing is not performed, the capture of pacing pulses may be automatically verified by microcontroller 60. In this regard, any loss of capture of pacing pulses is detected and backup pulses are delivered. Capture detection is preferably performed on a beat-by-beat basis. Capture detection is typically not necessary during far-field DAO pacing because the generally higher pulse magnitudes used during far-field pacing substantially ensure capture. A technique for implementing automatic capture verification during overdrive pacing is described in the aforementioned patent application of Bradley et al.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules) or high energy (11 to 40 joules), as controlled by the microcontroller 60. Such shocking pulses are applied to the heart of the patient through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generated under the control of AF suppression unit 101. The fibrillation shocks are generated under the control of other components of microcontroller 60, not separately shown. Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As will be explained below, cardioversion shocks and far-field DAO pacing pulses are smoothed to reduce pain. Accordingly, shocking circuit 116 includes circuitry for smoothing the cardioversion shocks (as well as for smoothing defibrillation shocks) and atrial pulse generator 70 (as well as ventricular pulse generator 72) likewise includes pulse-smoothing circuitry. Shocking circuit 116 and pulse generators 70 and 72 additionally include switching circuitry for selectively enabling or disabling pulse smoothing. Techniques for smoothing cardioversion shocks are set forth in U.S. patent application Ser. Nos. 09/967,652 and 09/967,647, both of Kroll et al., entitled "System And Method Of Generating A Low-Pain Multi-Step Defibrillation Waveform For Use In An Implantable Cardioverter/Defibrillator (ICD)", and both filed Sep. 28, 2001, which are incorporated herein by reference. These and other smoothing techniques may generally be applied to the smoothing of the far-field pacing pulses as well.

Referring to the remaining figures, flow charts provide an overview of the operation and novel features of stimulation device 10 as configured in accordance with exemplary embodiments of the invention. In these flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Tiered AF Suppression

FIG. 3 illustrates pertinent components of tiered AF suppression system 101 of FIG. 2. The AF suppression system includes an AF detection unit 152 for detecting the onset of AF and a cardioversion shock unit 154 for delivering one or more cardioversion shocks following detection of AF. The suppression system also includes a far-field DAO unit 156 for controlling delivery of DAO pacing during a far-field DAO phase immediately following the cardioversion shocks and a near-field DAO unit for controlling delivery of DAO pacing pulses at other times. The suppression system also includes a pulse smoothing unit 160 for smoothing both cardioversion shocks and far-field DAO pacing pulses. A DAO pulse tapering unit 162 provides for a gradual reduction of DAO pacing pulse magnitudes and a PPI unit 164 provides for delivery of PPI pulses prior to other pulses for the purposes of reducing pain. A tiered therapy controller 166 controls operation of the various components of the AF suppression system.

As shown in the FIG. 2, the AF suppression system is preferably implemented as a component of microcontroller 60. However, all or a portion of the AF suppression system may be implemented separately from the microcontroller. When implemented as a portion of the microcontroller, the various components of the AF suppression system operate to control other components of the implanted device, such as shocking circuit 116 and switch 74, to generate the pacing or shocking pulses, to smooth the pulses, etc. If implemented separately from a microcontroller, the various components of AF suppression system may include circuitry for actually generating and manipulating the various pacing and shocking pulses. As can be appreciated, the AF suppression system can be implemented in accordance with a wide range of different physical embodiments and no attempt is made herein to illustrate or enumerate all possible embodiments.

Figure 4:
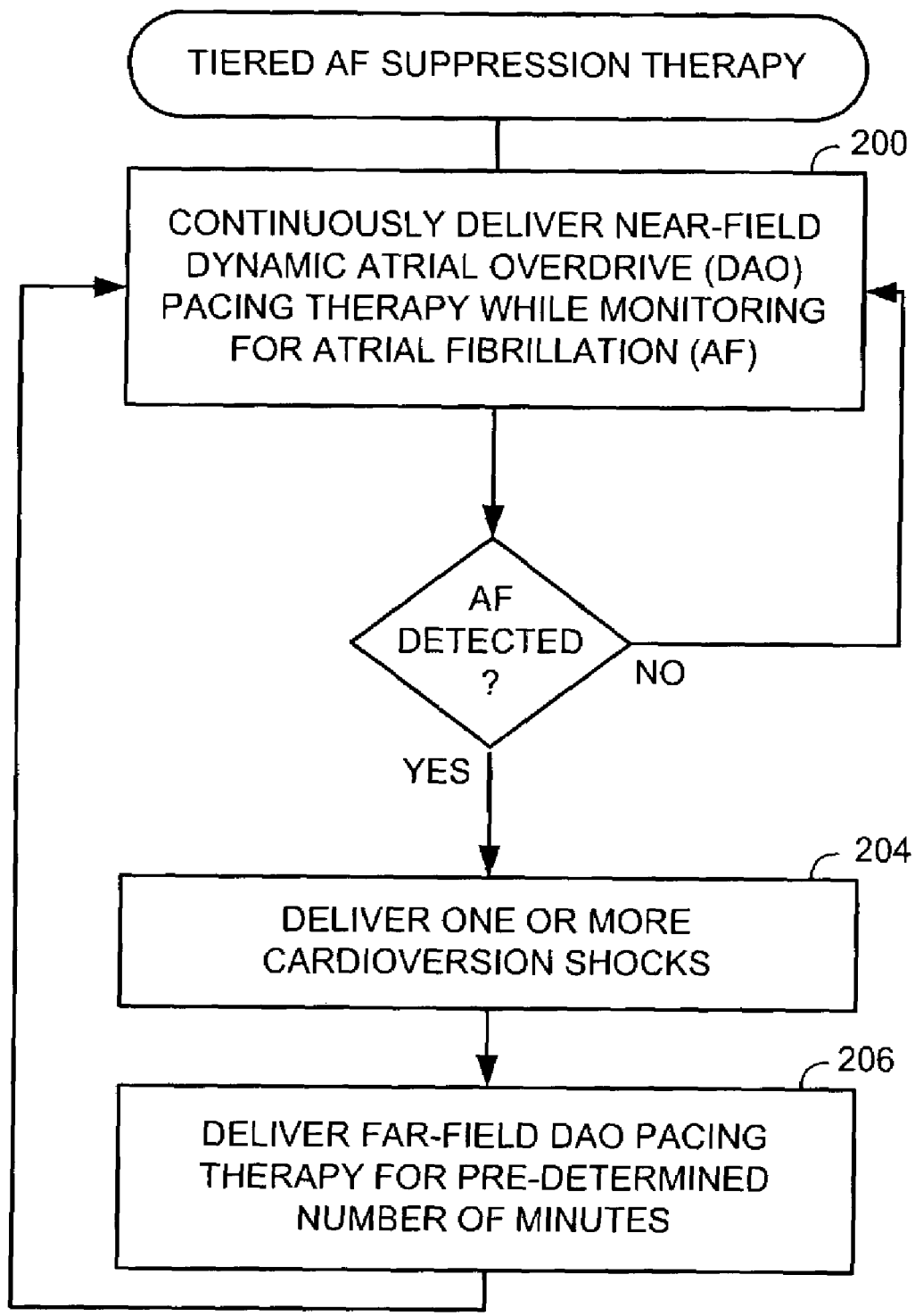
FIG. 4 is a flow chart providing an overview of the operation of an exemplary embodiment of the invention particularly illustrating the manner by which the tiered AF suppression system of FIG. 3 coordinates the delivery of cardioversion therapy and overdrive pacing therapy.

Referring to FIGS. 4 and 5, an overview of an exemplary method for achieving AF suppression using the components of FIG. 3 will now be described. Initially, at step 200 of FIG. 4, the AF suppression system delivers near-field DAO pacing therapy while monitoring intracardiac electrogram (IEGM) signals to detect the onset of AF. AF may be detected, for example, based on the heart rate, i.e., if the atrial heart rate exceeds some threshold value such as 150 beats per minute (bpm), AF is assumed. Other techniques for detecting AF are described in U.S. Pat. No. 6,097,983, to Strandberg, entitled "Cardiac Event Detecting System for a Heart Stimulator", which is incorporated by reference herein. Near-field DAO is performed in accordance with otherwise standard DAO techniques using relatively low voltage pacing pulses, on the order of 5 volts, delivered between tip and ring electrodes within the atria, such as right atrial tip electrode 22 and right atrial ring electrode 23. All near-field pacing pulses have substantially the same voltage as one another and, because the voltage is relatively low, smoothing is typically not performed.

Briefly, with standard conventional DAO pacing techniques (as described, for example, in U.S. Pat. No. 6,519,493 cited above), the DAO system detects the intrinsic atrial rate of the patient then paces the atria at a rate 5 to 10 bpm faster. While overdrive pacing the atria, the system searches IEGM signals to detect intrinsic breakthrough beats, i.e. atrial beats that arise despite overdrive pacing. Whenever two consecutive atrial breakthrough beats arise, the system increases the overdrive rate, typically by another 5 bpm. Eventually, if no breakthrough beats are detected, the overdrive a rate is decremented by, for example, 5 bpm. In this manner, the overdrive rate is maintained, on average, slightly above the intrinsic atrial rate of the patient. As explained above, this helps prevent the onset of AF and other tachycardias.

If AF nevertheless arises, the AF suppression system delivers one or more cardioversion shocks, at step 204, and then immediately begins delivering far-field DAO pacing therapy, at step 206, for about two minutes before resuming near-field DAO therapy again, at step 200. The cardioversion shocks delivered at step 204 are preferably smoothed to reduce patient pain. The far-field overdrive pacing pulses are also preferably smoothed to reduce patient pain and are gradually reduced in magnitude from a relatively high voltage such as 25 volts (also referred to herein as the maximum far-field pulse output level) down to a lower voltage such as 5 volts (also referred to herein as the minimum far-field pulse output level). Moreover, PPI pain reduction pulses are preferably delivered prior to each far-field pacing pulse.

Far-field overdrive pacing is delivered using electrodes selected to capture as much as the atria as possible without unduly pacing the ventricles. In one example, far-field pacing is delivered using the right atrial coil electrode with the device housing as the return electrode. In another example, a ring electrode 27 or coil electrode 28 amounted in the coronary sinus is used as the return electrode in combination with the right atrial coil. By using electrodes that are more widely spaced than the atrial tip and ring electrodes than used in connection with near-field pacing and by using greater voltages than used in connection with near-field pacing, the far-field pacing pulses thereby capture a larger portion of the atria so as to more effectively resynchronize the atria to prevent the reoccurrence of AF during the crucial period of time immediately following delivery of the cardioversion shock. By smoothing the far-field pulses and by applying pre-pulse in addition pulses, pain that might otherwise occur during far-field pacing is thereby reduced. Far-field overdrive pacing is performed for between one to three minutes and preferably for about two minutes. Far-field pacing is described in greater detail below with reference to FIGS. 6 and 7.

Hence, three phases or tiers of AF suppression are provided: cardioversion therapy; a far-field DAO pacing therapy; and near-field DAO pacing therapy. This sequence is shown in FIG. 5. Briefly, a smoothed cardioversion shock 208 is delivered in response to the detection of AF (with the AF itself not shown). Then smoothed, far-field pacing pulses 210 are delivered while the magnitude or amplitude of the pacing pulses is gradually reduced or tapered. Finally, non-smoothed, non-tapered near-field pacing pulses 212 are delivered during the near-field phase. Although not shown, during the cardioversion phase two or more cardioversion shocks may be delivered with potentially differing pulse magnitudes. PPI pulses may be delivered prior to each cardioversion shock and prior to each far-field pulse. In the unlikely event that AF nevertheless reoccurs during far-field DAO pacing, far-field DAO is immediately deactivated and additional cardioversion shocks are delivered.

Within both the far-field phase and the near-field phases shown in FIG. 5, pairs of intrinsic breakthrough beats 214 are shown. Prior to the detection of a pair of breakthrough beats, the overdrive pacing rate is gradually decreased in accordance with the standard DAO pacing techniques summarized above. Within FIG. 5, the overdrive rate is shown to decrease slightly with each overdrive pacing pulse. In preferred implementations, however, the overdrive rate only decreases following some predetermined number of pacing pulses or following some predetermined period of time.

Finally with regard to FIG. 5, note that the shapes of the pulses and shocks shown therein are not intended to represent the actual shapes of such events but instead provide a stylized representation to aid in understanding the invention.

Figure 6:
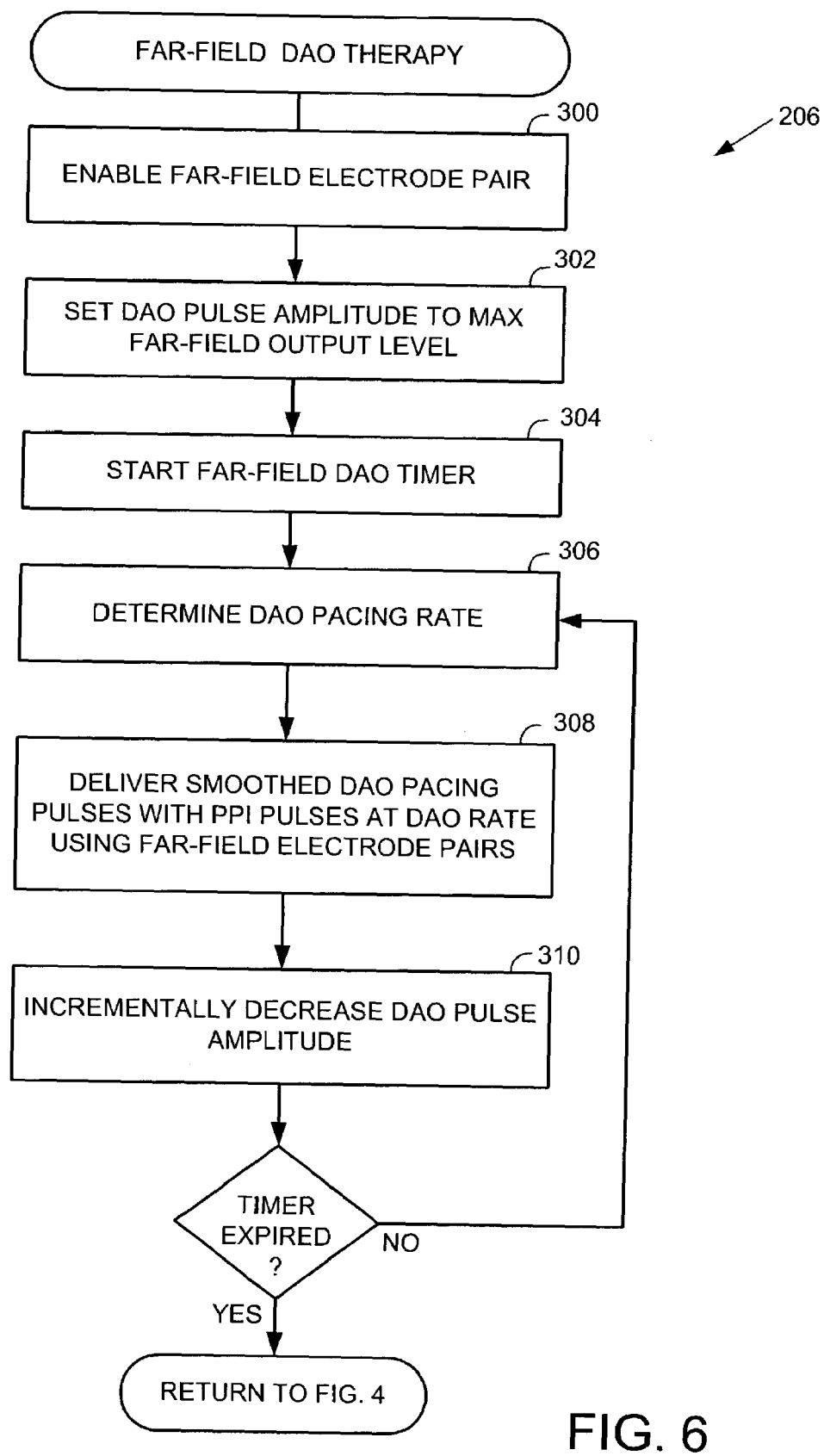
FIG. 6 is a flow chart providing individual steps performed by the AF suppression system of FIG. 3 to implement far-field DAO with PPI pulses.

Referring to FIGS. 6 and 7, far-field DAO therapy will now described in somewhat greater detail. Initially, at step 300, the AF suppression system activates or enables the far-field electrode pair for use in performing far-field DAO pacing, such as the aforementioned combination of the atrial coil electrode 38 (FIG. 1) and the device housing. The far-field electrode pair is enabled by sending control signals to configuration switch 74 (FIG. 2) for connecting the selected far-field electrodes with the various pulse generators and sense amplifiers of FIG. 2. Details regarding techniques for selectively enabling different electrode combinations are set forth in U.S. Pat. No. 6,456,876 to Kroll, entitled "Dual-Chamber Implantable Cardiac Stimulation System And Device With Selectable Arrhythmia Termination Electrode Configurations And Method." Then, at step 302, the system sets the DAO pulse magnitude to the maximum far-field output level. A far-field DAO timer is activated, at step 304, which is preset to, for example, two minutes. At step 306, the system determines the initial overdrive rate for use during DAO. The initial DAO rate may be initially determined by detecting the intrinsic atrial rate of the patient, then setting the overdrive rate to 5 or 10 bpm higher. Alternatively, since AF has just occurred, DAO may be programmed to begin at some predetermined high rate, such as 100 bpm.

At step 308, the system delivers smoothed DAO pacing pulses at the current DAO rate with each pulse preceded by a PPI pain reduction pulse. Both the pacing pulses and the PPI pulses are preferably delivered using the far-field electrode pairs. Note that the PPI pulses need not be delivered by the same electrodes as the pacing. However, to be effective, the PPI should be perceived (but without being painful) and so it is preferably delivered using far-field electrodes. The can is an effective electrode for the PPI since the chest muscle and skin are very sensitive to electrical stimulation and thus a PPI delivered using the can as a return electrode is easily perceived. In general, PPI pulses may be delivered in accordance with otherwise conventional techniques such as those set forth in U.S. Pat. No. 6,438,418 to Swerdlow, et al. entitled "Method and Apparatus for Reduction of Pain from Electric Shock Therapies". Still other techniques for reducing pain may be employed such as those set forth in U.S. Pat. Nos. 5,314,448 and 5,366,485 both to Kroll et al. Alternatively, or additionally, TENS or NEAP techniques are employed using the implanted device to reduce pain. The application of TENS and NEAP techniques for use within implantable devices is described in U.S. Pat. No. 6,208,902 to Boveja, entitled "Apparatus and Method for Adjunct (Add-On) Therapy for Pain Syndromes Utilizing an Implantable Lead and an External Stimulator". Each of the aforementioned patents is incorporated by reference herein.

At step 310, the system incrementally decreases the pulse magnitude from the initial maximum far-field output level down to a minimum far-field output level, which may be set to, for example, the near-field pulse output level. Preferably, the amount of incremental decrease performed at step 310 is selected such that, over a period of two minutes, the magnitude of the far-field DAO pulses decreases graduated from the maximum to the minimum far-field output levels. In any case, assuming that the far-field timer has not yet expired, processing continues, at step 306, to determine a new DAO pacing rate and to continue delivering smoothed DAO pacing pulses, at step 308. The smoothed far-field pacing pulses 210 are shown in FIG. 7 along with lower-amplitude PPI pulses 216. FIG. 7 also shows a pair of intrinsic beats 214, which trigger an automatic increase in the overdrive rate as explained above. Once the far-field timer expires, processing returns to FIG. 4. In addition, although not shown in FIG. 6 or 7, should AF nevertheless reoccur during a far-field overdrive pacing, the overdrive pacing is immediately suspended and additional cardioversion shocks are delivered.

Thus, FIGS. 4–7 illustrate exemplary methods for achieving AF suppression using the components of FIG. 3. Alternative techniques may be implemented as well. For example, far-field pacing pain reduction techniques may be selectively activated depending upon the particular electrode pair that is used for far-field pacing. In this regard, pulse smoothing and PPI pulses may be activated, for example, only if the device housing is used as the return electrode but not otherwise. In addition, far-field pain reduction techniques may be deactivated, for example, once the far-field pulse magnitude has dropped below some predetermined level, such as 15 volts. Pulse tapering may also be selectively activated, for example, depending upon the particular electrode pair used for far-field pacing, with tapering only employed if the device housing is used as the return electrode. In this regard, if the device housing is not used as the return electrode, then substantially uniform pulse magnitudes may be employed, for example, throughout far-field pacing with the uniform far-field pulse magnitudes being higher than the subsequent near-field levels but lower than the aforementioned maximum far-field pulse magnitude levels. For patients without AF, the two levels of DAO pacing may nevertheless be exploited, with the more aggressive far-field DAO pacing employed whenever other atrial tachycardias have occurred (or there is a risk of such tachycardias occurring) and with near-field DAO employed otherwise.

As can be appreciated, a wide variety of techniques can be implemented consistent with the principles the invention and no attempt is made herein to describe all possible techniques. Moreover, although described primarily with reference to atrial overdrive pacing, the techniques of the invention may be exploited, modified as needed, for use with ventricular overdrive pacing. In addition, although described primarily with reference to an example wherein the implanted device is a defibrillation/pacer, principles of the invention are applicable to other implantable cardiac stimulation devices as well such as pacemakers without defibrillation capability. Moreover, while the invention has been described in the context of dynamic overdrive pacing, it will be apparent to those skilled in the art that the invention may also be carried out using more conventional overdrive pacing techniques. For example, the overdrive pacing pulses may be delivered at a preset overdrive pacing rate, such as 80 ppm or the like.

The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device for implant within a patient, wherein the device has an overdrive pacing system and a cardioversion system, wherein the overdrive pacing system includes a far-field overdrive delivery system and a near-field overdrive delivery system, a method comprising:
   delivering cardioversion therapy to the heart of the patient using the cardioversion system; and
   delivery dynamic overdrive pacing therapy to the heart using the overdrive pacing system substantially immediately following the cardioversion therapy, wherein delivering dynamic overdrive pacing therapy comprises:
   delivering dynamic, far-field overdrive therapy during a first overdrive pacing phase; and
   delivering dynamic, near-field overdrive therapy during a second overdrive pacing phase;
   wherein the first overdrive pacing phase is a predetermined, brief period of time and the second overdrive pacing phase is a period of time substantially greater than the first overdrive pacing phase.

2. The method of claim 1 wherein the device is connected to a plurality of electrodes and wherein delivering far-field overdrive therapy comprises:
   delivering overdrive pacing pulses using a pair of electrodes selected so that the pacing pulses are captured throughout substantially all of the atria.

3. The method of claim 2 wherein the device includes a housing and wherein the plurality of electrodes include a right atrial coil electrode and wherein delivering far-field overdrive therapy comprises:
   delivering overdrive pacing pulses between the right atrial coil electrode and the device housing.

4. The method of claim 2 wherein the plurality of electrodes include a right atrial coil electrode and a ring electrode mounted near the proximal coronary sinus and wherein delivering far-field overdrive therapy comprises:
   delivering overdrive pacing pulses between the right atrial coil electrode and the ring electrode mounted near the proximal coronary sinus.

5. The method of claim 1 wherein delivering far-field overdrive therapy comprises:
   delivering overdrive pacing pulses while gradually reducing a magnitude of the pacing pulses.

6. The method of claim 1 wherein delivering far-field overdrive therapy comprises:
   delivering overdrive pacing pulses having a pulse shape selected to reduce patient pain.

7. The method of claim 6 wherein delivering overdrive pacing pulses having a pulse shape selected to reduce patient pain comprises:
   delivering smoothed overdrive pacing pulses.

8. The method of claim 1 wherein delivering far-field overdrive therapy comprises:
   delivering a series of pairs of pulses each including a pre-pulse inhibition (PPI) pulse and a subsequent overdrive pacing pulse.

9. The method of claim 1 wherein delivering far-field overdrive therapy during a first overdrive phase comprises:
   delivering far-field overdrive therapy for between one and three minutes.

10. The method of claim 1 wherein delivering dynamic overdrive pacing therapy comprises:
    delivering dynamic atrial overdrive (DAO) therapy.

11. An implantable cardiac stimulation device for implant within a patient, a system comprising:
    a cardioversion shock delivery system;
    a dynamic overdrive pacing system including a far-field overdrive pacing system and a near-field overdrive pacing system; and a control system operative to control the cardioversion system to generate a cardioversion shock for delivery to the heart of the patient and to control the dynamic overdrive pacing system to generate dynamic overdrive pulses for delivery to the heart of the patient substantially immediately following the cardioversion shock and to control the far-field overdrive pacing system to deliver far-field overdrive pacing therapy for a predetermined, brief period of time and to control the near-field overdrive pacing system to deliver near-field overdrive pacing therapy for a period of time substantially greater than the predetermined, brief period of time.

12. In an implantable cardiac stimulation device for implant within a patient, wherein the device has a far-field overdrive pacing system, a near-field overdrive pacing system and a cardioversion system, a method comprising:

delivering cardioversion therapy to the heart of the patient using the cardioversion system;

delivering far-field overdrive pacing therapy to the heart using the far-field overdrive pacing system following the cardioversion therapy; and delivering near-field overdrive pacing therapy to the heart using the near-field overdrive pacing system following the far-field overdrive pacing therapy;

wherein the far-field overdrive pacing therapy is delivered for a predetermined, brief period of time and the near-field overdrive pacing therapy is delivered for a period of time substantially greater than the predetermined, brief period of time.

13. The method of claim 12 wherein the device is connected to a plurality of electrodes and wherein delivering far-field overdrive therapy comprises:

delivering overdrive pacing pulses using a pair of electrodes selected so that the pacing pulses are captured throughout substantially all of the atria.

14. The method of claim 13 wherein the device includes a housing and wherein the plurality of electrodes include a right atrial coil electrode and wherein delivering far-field overdrive therapy comprises:

delivering overdrive pacing pulses between the right atrial coil electrode and the device housing.

15. The method of claim 13 wherein the plurality of electrodes include a right atrial coil electrode and a ring electrode mounted near the proximal coronary sinus and wherein delivering far-field overdrive therapy comprise:

delivering overdrive pacing pulses between the right atrial coil electrode and the ring electrode mounted near the proximal coronary sinus.

16. An implantable cardiac stimulation device for implant within a patient, a system comprising:

a lead system configured for implant within the patient;

a cardioversion shock delivery system operative to deliver a cardioversion shock via the lead system;

a far-field overdrive pacing system operative to generate overdrive pacing pulses for far-field delivery to the patient via the lead system;

a near-field overdrive pacing system operative to generate overdrive pacing pulses for near-field delivery to the patient via the lead system; and a control system operative to control the cardioversion system to generate a cardioversion shock for delivery to the heart of the patient and to control the far-field overdrive pacing system to deliver far-field overdrive pacing therapy for a predetermined, brief period of time to the heart of the patient following the cardioversion shock and to control the near-field overdrive pacing system to deliver near-field overdrive pacing therapy for a period of time substantially greater than the predetermined, brief period of time to the heart of the patient following the far-field therapy.

17. The device of claim 16, wherein:

the far-field overdrive pacing system is operative to generate dynamic overdrive pacing pulses.

* * * * *